US009725733B2

(12) United States Patent
Matsunaga et al.

(10) Patent No.: US 9,725,733 B2
(45) Date of Patent: Aug. 8, 2017

(54) POLYNUCLEOTIDE ENCODING NF-YB DERIVED FROM JATROPHA AND USE THEREOF

(71) Applicant: OSAKA UNIVERSITY, Osaka (JP)

(72) Inventors: Sachihiro Matsunaga, Osaka (JP); Tsutomu Kohinata, Osaka (JP); Kiichi Fukui, Osaka (JP); Satoshi Tabata, Chiba (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 15/235,289

(22) Filed: Aug. 12, 2016

(65) Prior Publication Data

US 2017/0044567 A1    Feb. 16, 2017

Related U.S. Application Data

(63) Continuation of application No. 13/639,522, filed as application No. PCT/JP2011/058026 on Mar. 30, 2011, now Pat. No. 9,447,426.

(30) Foreign Application Priority Data

Apr. 9, 2010  (JP) ................. 2010-090618
Dec. 8, 2010  (JP) ................. 2010-273463

(51) Int. Cl.
  *C12N 15/29*   (2006.01)
  *C12N 15/82*   (2006.01)
  *C07K 14/415*  (2006.01)

(52) U.S. Cl.
  CPC ........ *C12N 15/8273* (2013.01); *C07K 14/415* (2013.01)

(58) Field of Classification Search
  None
  See application file for complete search history.

(56) References Cited

U.S. PATENT DOCUMENTS

| | | | |
|---|---|---|---|
| 9,447,426 | B2 | 9/2016 | Matsunaga et al. |
| 2005/0214808 | A1 | 9/2005 | Umezawa et al. |
| 2007/0174937 | A1 | 7/2007 | Umezawa et al. |
| 2008/0040973 | A1 | 2/2008 | Nelson et al. |
| 2009/0205079 | A1 | 8/2009 | Kumar et al. |

FOREIGN PATENT DOCUMENTS

| | | |
|---|---|---|
| JP | 2005-253395 | 9/2005 |
| JP | 2009-536029 | 10/2009 |
| JP | 2009-540830 | 11/2009 |
| WO | 2008/002480 | 1/2008 |
| WO | 2009/138535 | 11/2009 |
| WO | 2011/125748 | 10/2011 |

OTHER PUBLICATIONS

Sato et al. (DNA Research pp. 1-12, (2010)) (advanced publication Dec. 13, 2010).*
U.S. Appl. No. 13/643,396 to Kiichi Fukui et al., filed Oct. 25, 2012.
International Search Report for PCT/JP2011/058026, mailed Jun. 28, 2011.
Li et al., "The *Arabidopsis* NFYA5 Transcription Factor is Regulated Transcriptionally and Posttranscriptionally to Promote Drought Resistance," *The Plant Cell*, vol. 20, pp. 2238-2251, 2008.
Nelson et al., "Plant Nuclear Factor Y(NF-Y)B Subunits Confer Drought Tolerance and Lead to Improved Corn Yields on Water-Limited Acres," *PNAS*, vol. 104, No. 42, pp. 16450-16455, 2007.
Shibagaki et al., "Genetic engineering of Jatropha curcas L. for drought resistance," *Abstracts of the Annual Meeting of the Society for Biotechnology*, vol. 61, pp. 205, 2009, along with an English language translation.
Stephenson et al., "Genome-Wide Identification and Expression Analysis of the NF-Y Family of Transcription Factors in *Triticum aestivum*," *Plant Mol. Biol.*, vol. 65, No. 1-2, pp. 77-92, 2007.
Siefers et al., "Tissue-Specific Expression Patterns of Arabidopsis NF-Y Transcription Factors Suggest Potential for Extensive Combinatorial Complexity," *Plant Physiol.*, vol. 149, No. 2, pp. 625-641, 2009.
International Search Report for PCT/JP2011/074513, mailed Dec. 6, 2011.
Rubio et al., "The Coenzyme A Biosynthetic Enzyme Phosphopantetheine Adenylyltransferase Plays a Crucial Role in Plant Growth, Salt/Osmotic Stress Resistance, and Seed Lipid Storage," *Plant Physiol.* 148(1):546-556, 2008.
Kupke et al., "4'-Phosphopantetheine and Coenzyme A Biosynthesis in Plants," *J. Biol. Chem.* 278(40):38229-38237, 2003.
Akbar et al. (European Journal of Scientific Research, vol. 29, No. 3 (2009), pp. 396-403).
Chan et al. (GenBank Accession No. XP_002521564, Aug. 6, 2009).
Office Action issued for U.S. Appl. No. 13/643,396, mailed Aug. 14, 2014.
"Jatropha Oil Extraction. Methods and Devices for Extracting Jatropha Oil", http://www.jatrophaoilextraction.com/, 2008.
Office Action issued in Philippines Patent Appl. No. 1/2012/501925, mailed May 4, 2016.
Masiero et al. (JBC vol. 277, No. 29, Issue of Jul. 19, pp. 26429-26435, 2002).
Guo et al. (2004, Proc. Natl. Acad. Sci. USA 101: 9205-9210).
Achten et al. (Biomass and Bioenergy 32 (2008) 1063-1084.
Sato et al. (DNA Research pp. 1-12, (2010)).
Sato et al. DNA Res. Feb. 2011; 18(1): 65-76—advance publication Dec. 13, 2010.

* cited by examiner

*Primary Examiner* — Elizabeth McElwain
*Assistant Examiner* — Charles Logsdon
(74) *Attorney, Agent, or Firm* — Greenblum & Bernstein, P.L.C.

(57) ABSTRACT

By analyzing a *Jatropha* genome, NF-YB-encoding genes of SEQ ID NOs: 1 to 11, fragments of NF-YB-encoding genes of SEQ ID NOs: 12 and 13, and genes relating thereto were found. By transforming *Jatropha* with these NF-YB-encoding genes and the like, it is possible to overexpress a NF-YB polypeptide and so on, and to significantly improve the productivity of protein synthesis involved by the NF-YB polypeptide, and to significantly improve the dry stress resistance, for example. As a result, it is possible to create dry stress resistant *Jatropha* capable of ensuring high growth even under water deficient conditions.

6 Claims, 2 Drawing Sheets

SEQUENCE LISTING

```
<160> NUMBER OF SEQ ID NOS: 40

<210> SEQ ID NO 1
<211> LENGTH: 612
<212> TYPE: DNA
<213> ORGANISM: Jatropha sp.

<400> SEQUENCE: 1
atggcggatt ccgacaatga atctggagga cacaacaata acgcgaacag cgaactgtcg      60
gctcgcgaac aggacaggtt tttgccaatc gctaacgtta gcagaataat gaaaaaagct     120
ttgccggcca acgcgaagat ctcgaaagat gcaaaagaaa cggtgcagga gtgtgtatct     180
gaatttatca gctttattac cggagaagct tccgataagt gccagcgcga aaagcgaaag     240
acgattaacg gcgacgatct gctatgggct atgacgacgt taggttttga agagtacgtt     300
gagcctttaa agatttattt gcagaagtat agggagatgg aaggggagaa gagttctatg     360
ggaagacaag gagagaaaga tggtgctggt gggtctggtg gtggcggtgc cgccgcaggc     420
ggtggtgggt ccggtggagg agttagttct agtgcaggag gaggagctgg aggtggaggg     480
tttaatggcg gtggtcaagg gatgtatggt gggatgatga tgatgggaca tcatcaagga     540
cacatgtacg gctccggtgg gtatcatcag caaatgggta tcggaaaagg tggctccggc     600
aattcaaggt ag                                                         612

<210> SEQ ID NO 2
<211> LENGTH: 525
<212> TYPE: DNA
<213> ORGANISM: Jatropha sp.

<400> SEQUENCE: 2
```

```
atggttgaca atgcaagcaa taattcagac aaatcatacc aaaagtacaa ctttggagga    60
gctagtagtg gttcaggaga agatggcata ataaaggagc aagatagatt gcttccaata   120
gctaatgttg ggagaatcat gaagcaaatt cttcctccaa atgcaaaaat ctcaaaagaa   180
gctaaagaaa caatgcaaga atgtgtatct gagttcataa gctttgtaac aggtgaagca   240
tcagataaat gtcacaaaga gaagcgaaag actgttaatg gagatgatat tgttgggct    300 cttgctactt tagggtttga tgactacgca gagccactca agaggtattt gcatagatac   360
agagagcaag aaggagagag agctagcaat aaggggagca acaatgaaga aaatgatgat   420
tcctcgaatt gcagaggcga tcagccatgg aaatctgcgg ttcctagtgc tgctccattt   480
cagtttgatg caagcaataa cagttctgtt tccaggcgat tttga                    525
```

<210> SEQ ID NO 3
<211> LENGTH: 666
<212> TYPE: DNA
<213> ORGANISM: Jatropha sp.

<400> SEQUENCE: 3

```
atggaagaag agagccatgc cagtgctcca aatggcctaa atagaggaag cccagaaagc    60
ccatgtttaa agaacaataa caaaaataac aacaatggca gcagcaacaa caacaataat   120
aataaagagc aggatcgctt ccttcctata gcaaatgttg ggaggataat gagaaagta    180 agccccgcaa atgggaaaat atccaaagat gcgaaagaga cggttcaaga atgcgtttct   240
gagttcatta gcttcgtaac aggagaagct tcagataaat gccaaagaga aaaagaaag    300 accattaatg gagatgacat catttgggca ataacaacta taggtttcga agattacgtt   360 gttccccta aaacatatct cgtcaaatat cgagaggttg aaggagaaaa gctcaatatc   420
ccaaagcaac aaaggacaga acataggtta caacaacatc aacagccaaa acaagaacaa   480
caagaacaaa gtttactacc ttacaatagt gtatattcct ctaccagcag tcttatgtct   540
caaccaccat ttgtggctgc tgatcaacca ttttccttaa cattttctcc taattccatt   600
caaaaacagc tacagcaaca agatcaaatt gattcaattg ggcattggca agatatgaag   660
ttataa                                                              666
```

<210> SEQ ID NO 4
<211> LENGTH: 363
<212> TYPE: DNA
<213> ORGANISM: Jatropha sp.

<400> SEQUENCE: 4

```
atgaagcaaa tttttgcctcc taatgcaaaa atctcaaaag aagctaaaga aactatacaa    60
gaatgcgttt ctgagttcat tagttttgtg accagtgaag cctctgggaa gtgtcgaaag   120
gaaagaggga agactgtcaa tggagatgat atttgttggg ctatgggagc tctagggttt   180
gatgactatg cagagccttt aagaaggtac ttacaaagat atagggaaat agaaggagat   240
agagctaatc aagagaaggg aagcagtagc aataataata ctattactga agaaaatcga   300
gctccattga agtttgaccc agttgataag aggaatagct ctagaagttc aaggccatct   360
tag                                                                 363
```

<210> SEQ ID NO 5
<211> LENGTH: 531
<212> TYPE: DNA
<213> ORGANISM: Jatropha sp.

<400> SEQUENCE: 5

```
atggctggaa aaagaaacca ataaccagc cctatcggaa gcccttgtc agggaatatc    60 tctgatagct cttccaaaga gcaagaccga tttctcccta tcgccaacgt tagccgtatc   120
atgaaaaaat cacttcctgc aaatgcaaaa atatccaaag aagctaaaga aaccgttcaa   180
gaatgtgttt ctgagttcat aagcttcatc accggtgaag cctccgataa gtgtcaaaga   240 gaaaaagaa agaccattaa tggcgacgat cttttatggg ctatgactac actagggttt   300
gaaaattatg tgggtccgtt aaagatttat ctcaacaaat atagaaaac tgaaggagag    360 aaaaattcta tggctagaca agaagatcaa tctccgcttg caactaatga cgaaattaac   420
aaagtaaata gttcttttc aactgaggtt gacttgcaga cctttaatgg cggattttat    480
tcacttgggg cgcaagtaat tactcctaaa agcggctatg gatataactg a            531
```

<210> SEQ ID NO 6
<211> LENGTH: 402
<212> TYPE: DNA
<213> ORGANISM: Jatropha sp.

<400> SEQUENCE: 6

```
atggctgaga acccaacaag tccagcagga gggagccatg agagcggtgg tgagcagagc    60
ccgcactctg gagtgaggga acaggatagg tacctgccta ttgccaacat aagcaggatc   120
atgaagaagg ctttgcctgc caatggaaaa attgctaaag atgctaagga tactgtgcag   180
gaatgtgtct ctgaatttat tagctttatt accagcgagg cgagtgataa gtgtcagaag   240
gagaaaagaa agacaatcaa tggagatgat ttgttgtggg cgatggcaac tctaggcttt   300
gaggactata ttgaaccact taaggtgtac cttgctaggt acagggaggt aactaatctt   360
tcacttttgg aaacatgtgc tttttttct gtatatgctt ga                       402
```

<210> SEQ ID NO 7
<211> LENGTH: 411
<212> TYPE: DNA
<213> ORGANISM: Jatropha sp.

<400> SEQUENCE: 7

```
atggcgacgg aggcaccacc ggcaagccct ggcggtggca gccatgagag cggcgaacac    60 agccccccgct ctaactctaa ttttcgtgaa caagataggt acctgcccat cgccaatatt   120
agccggatca tgaagaaggc tcttcctgca atggtaaga tcgctaagga tgctaaggaa   180
actgttcagg aatgcgtctc tgagtttatc agtttcatca ccagcgaggc gagtgataag   240
tgtcagagag agaagaggaa gacaatcaat ggtgatgatt tgctatgggc tatggcgacg   300
ttaggttttg aggattatat cgatccgctt aagatttact tgtctcgata cagagaggtc   360
aacttaagct ttcaattttg gttgcaagtc gttttcgttt ttagtttatg a             411
```

<210> SEQ ID NO 8
<211> LENGTH: 471
<212> TYPE: DNA
<213> ORGANISM: Jatropha sp.

<400> SEQUENCE: 8

```
atggaaccca tggatattgt tggtaaatcg aaagaggatg cttcgctacc taaagcaact    60
atgaccaaaa ttattaaaga gatgttacct ccagacgttc gcgttgcaag agatgcacaa   120
gatcttttga tagagtgttg tgtagagttt ataaaccttg tatcatcaga gtccaatgaa   180
gtatgcagta aagaggagaa gcggacgatt gcgcctgagc atgtactcaa ggcgttagag   240
```

```
gttcttggtt ttggagagta catcgaagag gtttatgctg catacgagca acacaagctt    300
gagactatgg actcattaaa aggtggtaaa tggagcaatg gagcgagat gaccgaggaa    360 gaagcagtag cggagcagca aggatgtttt gctgaggcac gtgcaagaat gaatggaggt    420
gctattgccc caaagcaaca accagagact gaccgaagtt tagagagcta a            471

<210> SEQ ID NO 9
<211> LENGTH: 312
<212> TYPE: DNA
<213> ORGANISM: Jatropha sp.

<400> SEQUENCE: 9
atggagtcgg agaatgtgga aaaagtagta tcggaggcgg aggagttgcc gaaggctatt    60
gtgcgccgga tagtgaagga taagctctcc caatgctccc ccgacggcga cctcattgtc    120
cacaaagacg ctctcgtcgc tttctccgaa agtgcgagaa tcttcatcca ctatctttcc    180
gccacggcta acgatatatg caaggaatcg aggaggcaaa ccatcaacgc agacgatgtg    240
ttaaaggcgc ttgaagaaat tgaatttccc gagtttgttg agcctctcaa agcctccctt    300
aaaggcaagt ga                                                       312

<210> SEQ ID NO 10
<211> LENGTH: 369
<212> TYPE: DNA
<213> ORGANISM: Jatropha sp.

<400> SEQUENCE: 10
atgactactt taggatttga agagtatgtt gagcctctga agtttacttt gcagaggttc    60
agagaaatgg aagggagaa ggcagctgtg gggcgtgata agacgctcc aggtaatgga    120 gggccacgtg tacgggtctg gtggtggatt ctacaatcag atggccggtg gtattgggtt    180
ggcgaaaggt gcatcaacca tcagagacgc gtacatgtga atttcatctt acggctgcag    240
gaggtggtgg tgtctatgta catgtgtgta tatctgattt tggtgatggg aagatgatt    300 ggatcaacgg tggatgatga cgacgattat aataggaaat tatattatgc ctgtgccatt    360
ttaatttaa                                                           369

<210> SEQ ID NO 11
<211> LENGTH: 300
<212> TYPE: DNA
<213> ORGANISM: Jatropha sp.

<400> SEQUENCE: 11
atgagcaagc tagggtttga tgactacatt gaaccctga ctgtgtatct acaccgctat    60
cgggagatgg aaggggaccg tagctcgata agaagtgagc cattggtgaa gaggaatgtt    120
gagtttggtc cattaggggt tgcaactgct tttgcgccag cattccatat gtctcatcat    180
caccatgggt tttttggagg agctgcagcg gctatgggtg gatataccag ggatccttcc    240
aatgcaactt cttcacagca tgcattggcc aacggcgagt cgtttgggca gcacaaatga    300

<210> SEQ ID NO 12
<211> LENGTH: 292
<212> TYPE: DNA
<213> ORGANISM: Jatropha sp.

<400> SEQUENCE: 12
atgcctcgaa gtacagtcag atctctagcc aaaacgatcc tcaatgatga caccaatatt    60
cagaaagacg cactgacggc acttgtcaaa ggatctactg tctttatcag ctacttggct    120
```

```
tctcatgcga acgagatagc gcattcgaag aaaagaaaga caatcatgcc taacgacgtc    180
ttcgaggcgt tgaagattat cgaatatgat cgtttcacat cagatctaag ggaagagttt    240
ggcgaatttc cagcaaaaaa agttggaaag agtgtcgagg ctgtagacga tg            292
```

<210> SEQ ID NO 13
<211> LENGTH: 219
<212> TYPE: DNA
<213> ORGANISM: Jatropha sp.

<400> SEQUENCE: 13

```
ggtttgacaa ctacgctgag gctatagtta ggtatttaca taaatataga gaagctgaaa     60
gagagaaagc ttacaataat caaaacaaag ctaatccttc caatcaagaa aaagatgatg    120
acaatcaaga agccaactct aaaagtagta gcagtcaaga acagcagcag atcaatgaaa    180
caattccttc tacattggag tttagggttc ttgagaagg                           219
```

<210> SEQ ID NO 14
<211> LENGTH: 203
<212> TYPE: PRT
<213> ORGANISM: Jatropha sp.

<400> SEQUENCE: 14

```
Met Ala Asp Ser Asp Asn Glu Ser Gly Gly His Asn Asn Ala Asn
1               5                   10                  15

Ser Glu Leu Ser Ala Arg Glu Gln Asp Arg Phe Leu Pro Ile Ala Asn
            20                  25                  30

Val Ser Arg Ile Met Lys Lys Ala Leu Pro Ala Asn Ala Lys Ile Ser
        35                  40                  45

Lys Asp Ala Lys Glu Thr Val Gln Glu Cys Val Ser Glu Phe Ile Ser
50                  55                  60

Phe Ile Thr Gly Glu Ala Ser Asp Lys Cys Gln Arg Glu Lys Arg Lys
65                  70                  75                  80

Thr Ile Asn Gly Asp Asp Leu Leu Trp Ala Met Thr Thr Leu Gly Phe
                85                  90                  95

Glu Glu Tyr Val Glu Pro Leu Lys Ile Tyr Leu Gln Lys Tyr Arg Glu
            100                 105                 110

Met Glu Gly Glu Lys Ser Ser Met Gly Arg Gln Gly Glu Lys Asp Gly
        115                 120                 125

Ala Gly Gly Ser Gly Gly Gly Ala Ala Ala Gly Gly Gly Gly Ser
    130                 135                 140

Gly Gly Gly Val Ser Ser Ser Ala Gly Gly Gly Ala Gly Gly Gly Gly
145                 150                 155                 160

Phe Asn Gly Gly Gly Gln Gly Met Tyr Gly Gly Met Met Met Gly
                165                 170                 175

His His Gln Gly His Met Tyr Gly Ser Gly Gly Tyr His Gln Gln Met
            180                 185                 190

Gly Ile Gly Lys Gly Gly Ser Gly Asn Ser Arg
        195                 200
```

<210> SEQ ID NO 15
<211> LENGTH: 174
<212> TYPE: PRT
<213> ORGANISM: Jatropha sp.

<400> SEQUENCE: 15

Met Val Asp Asn Ala Ser Asn Asn Ser Asp Lys Ser Tyr Gln Lys Tyr

```
             1               5                  10                 15
        Asn Phe Gly Gly Ala Ser Ser Gly Ser Gly Glu Asp Gly Ile Ile Lys
                        20                 25                 30
        Glu Gln Asp Arg Leu Leu Pro Ile Ala Asn Val Gly Arg Ile Met Lys
                        35                 40                 45
        Gln Ile Leu Pro Pro Asn Ala Lys Ile Ser Lys Glu Ala Lys Glu Thr
         50                 55                 60
        Met Gln Glu Cys Val Ser Glu Phe Ile Ser Phe Val Thr Gly Glu Ala
         65                 70                 75                 80
        Ser Asp Lys Cys His Lys Glu Lys Arg Lys Thr Val Asn Gly Asp Asp
                        85                 90                 95
        Ile Cys Trp Ala Leu Ala Thr Leu Gly Phe Asp Asp Tyr Ala Glu Pro
                        100                105                110
        Leu Lys Arg Tyr Leu His Arg Tyr Arg Glu Gln Glu Gly Glu Arg Ala
                        115                120                125
        Ser Asn Lys Gly Ser Asn Asn Glu Glu Asn Asp Asp Ser Ser Asn Cys
                        130                135                140
        Arg Gly Asp Gln Pro Trp Lys Ser Ala Val Pro Ser Ala Ala Pro Phe
        145                150                155                160
        Gln Phe Asp Ala Ser Asn Asn Ser Ser Val Ser Arg Arg Phe
                        165                170
```

<210> SEQ ID NO 16
<211> LENGTH: 221
<212> TYPE: PRT
<213> ORGANISM: Jatropha sp.

<400> SEQUENCE: 16

```
        Met Glu Glu Ser His Ala Ser Ala Pro Asn Gly Leu Asn Arg Gly
         1                 5                  10                 15
        Ser Pro Glu Ser Pro Cys Leu Lys Asn Asn Lys Asn Asn Asn
                        20                 25                 30
        Gly Ser Ser Asn Asn Asn Asn Asn Lys Glu Gln Asp Arg Phe Leu
                        35                 40                 45
        Pro Ile Ala Asn Val Gly Arg Ile Met Lys Lys Val Ser Pro Ala Asn
         50                 55                 60
        Gly Lys Ile Ser Lys Asp Ala Lys Glu Thr Val Gln Glu Cys Val Ser
         65                 70                 75                 80
        Glu Phe Ile Ser Phe Val Thr Gly Glu Ala Ser Asp Lys Cys Gln Arg
                        85                 90                 95
        Glu Lys Arg Lys Thr Ile Asn Gly Asp Asp Ile Ile Trp Ala Ile Thr
                        100                105                110
        Thr Leu Gly Phe Glu Asp Tyr Val Val Pro Leu Lys Thr Tyr Leu Val
                        115                120                125
        Lys Tyr Arg Glu Val Glu Gly Glu Lys Leu Asn Ile Pro Lys Gln Gln
                        130                135                140
        Arg Thr Glu His Arg Leu Gln Gln His Gln Gln Pro Lys Gln Glu Gln
        145                150                155                160
        Gln Glu Gln Ser Leu Leu Pro Tyr Asn Ser Val Tyr Ser Ser Thr Ser
                        165                170                175
        Ser Leu Met Ser Gln Pro Pro Phe Val Ala Ala Asp Gln Pro Phe Ser
                        180                185                190
        Leu Thr Phe Ser Pro Asn Ser Ile Gln Lys Gln Leu Gln Gln Gln Asp
                        195                200                205
```

-continued

```
Gln Ile Asp Ser Ile Gly His Trp Gln Asp Met Lys Leu
    210                 215                 220
```

<210> SEQ ID NO 17
<211> LENGTH: 120
<212> TYPE: PRT
<213> ORGANISM: Jatropha sp.

<400> SEQUENCE: 17

```
Met Lys Gln Ile Leu Pro Pro Asn Ala Lys Ile Ser Lys Glu Ala Lys
1               5                   10                  15

Glu Thr Ile Gln Glu Cys Val Ser Glu Phe Ile Ser Phe Val Thr Ser
            20                  25                  30

Glu Ala Ser Gly Lys Cys Arg Lys Glu Arg Gly Lys Thr Val Asn Gly
        35                  40                  45

Asp Asp Ile Cys Trp Ala Met Gly Ala Leu Gly Phe Asp Asp Tyr Ala
    50                  55                  60

Glu Pro Leu Arg Arg Tyr Leu Gln Arg Tyr Arg Glu Ile Glu Gly Asp
65                  70                  75                  80

Arg Ala Asn Gln Glu Lys Gly Ser Ser Asn Asn Asn Thr Ile Thr
                85                  90                  95

Glu Glu Asn Arg Ala Pro Leu Lys Phe Asp Pro Val Asp Lys Arg Asn
            100                 105                 110

Ser Ser Arg Ser Ser Arg Pro Ser
            115                 120
```

<210> SEQ ID NO 18
<211> LENGTH: 176
<212> TYPE: PRT
<213> ORGANISM: Jatropha sp.

<400> SEQUENCE: 18

```
Met Ala Gly Lys Arg Asn Gln Ile Thr Ser Pro Ile Gly Ser Pro Leu
1               5                   10                  15

Ser Gly Asn Ile Ser Asp Ser Ser Lys Glu Gln Asp Arg Phe Leu
            20                  25                  30

Pro Ile Ala Asn Val Ser Arg Ile Met Lys Lys Ser Leu Pro Ala Asn
        35                  40                  45

Ala Lys Ile Ser Lys Glu Ala Lys Glu Thr Val Gln Glu Cys Val Ser
    50                  55                  60

Glu Phe Ile Ser Phe Ile Thr Gly Glu Ala Ser Asp Lys Cys Gln Arg
65                  70                  75                  80

Glu Lys Arg Lys Thr Ile Asn Gly Asp Asp Leu Leu Trp Ala Met Thr
                85                  90                  95

Thr Leu Gly Phe Glu Asn Tyr Val Gly Pro Leu Lys Ile Tyr Leu Asn
            100                 105                 110

Lys Tyr Arg Glu Thr Glu Gly Glu Lys Asn Ser Met Ala Arg Gln Glu
        115                 120                 125

Asp Gln Ser Pro Leu Ala Thr Asn Asp Gly Ile Asn Lys Val Asn Ser
    130                 135                 140

Ser Phe Ser Thr Glu Val Asp Leu Gln Thr Phe Asn Gly Gly Phe Tyr
145                 150                 155                 160

Ser Leu Gly Ala Gln Val Ile Thr Pro Lys Ser Gly Tyr Gly Tyr Asn
                165                 170                 175
```

<210> SEQ ID NO 19
<211> LENGTH: 133

<212> TYPE: PRT
<213> ORGANISM: Jatropha sp.

<400> SEQUENCE: 19

Met Ala Glu Asn Pro Thr Ser Pro Ala Gly Gly Ser His Glu Ser Gly
1               5                   10                  15

Gly Glu Gln Ser Pro His Ser Gly Val Arg Glu Gln Asp Arg Tyr Leu
            20                  25                  30

Pro Ile Ala Asn Ile Ser Arg Ile Met Lys Lys Ala Leu Pro Ala Asn
        35                  40                  45

Gly Lys Ile Ala Lys Asp Ala Lys Asp Thr Val Gln Glu Cys Val Ser
    50                  55                  60

Glu Phe Ile Ser Phe Ile Thr Ser Glu Ala Ser Asp Lys Cys Gln Lys
65                  70                  75                  80

Glu Lys Arg Lys Thr Ile Asn Gly Asp Asp Leu Leu Trp Ala Met Ala
                85                  90                  95

Thr Leu Gly Phe Glu Asp Tyr Ile Glu Pro Leu Lys Val Tyr Leu Ala
            100                 105                 110

Arg Tyr Arg Glu Val Thr Asn Leu Ser Leu Leu Glu Thr Cys Ala Phe
        115                 120                 125

Phe Ser Val Tyr Ala
    130

<210> SEQ ID NO 20
<211> LENGTH: 136
<212> TYPE: PRT
<213> ORGANISM: Jatropha sp.

<400> SEQUENCE: 20

Met Ala Thr Glu Ala Pro Pro Ala Ser Pro Gly Gly Gly Ser His Glu
1               5                   10                  15

Ser Gly Glu His Ser Pro Arg Ser Asn Ser Asn Phe Arg Glu Gln Asp
            20                  25                  30

Arg Tyr Leu Pro Ile Ala Asn Ile Ser Arg Ile Met Lys Lys Ala Leu
        35                  40                  45

Pro Ala Asn Gly Lys Ile Ala Lys Asp Ala Lys Glu Thr Val Gln Glu
    50                  55                  60

Cys Val Ser Glu Phe Ile Ser Phe Ile Thr Ser Glu Ala Ser Asp Lys
65                  70                  75                  80

Cys Gln Arg Glu Lys Arg Lys Thr Ile Asn Gly Asp Asp Leu Leu Trp
                85                  90                  95

Ala Met Ala Thr Leu Gly Phe Glu Asp Tyr Ile Asp Pro Leu Lys Ile
            100                 105                 110

Tyr Leu Ser Arg Tyr Arg Glu Val Asn Leu Ser Phe Gln Phe Trp Leu
        115                 120                 125

Gln Val Val Phe Val Phe Ser Leu
    130                 135

<210> SEQ ID NO 21
<211> LENGTH: 156
<212> TYPE: PRT
<213> ORGANISM: Jatropha sp.

<400> SEQUENCE: 21

Met Glu Pro Met Asp Ile Val Gly Lys Ser Lys Glu Asp Ala Ser Leu
1               5                   10                  15

Pro Lys Ala Thr Met Thr Lys Ile Ile Lys Glu Met Leu Pro Pro Asp

```
            20                  25                  30
Val Arg Val Ala Arg Asp Ala Gln Asp Leu Leu Ile Glu Cys Cys Val
                35                  40                  45
Glu Phe Ile Asn Leu Val Ser Ser Glu Ser Asn Glu Val Cys Ser Lys
 50                  55                  60
Glu Glu Lys Arg Thr Ile Ala Pro Glu His Val Leu Lys Ala Leu Glu
 65                  70                  75                  80
Val Leu Gly Phe Gly Glu Tyr Ile Glu Val Tyr Ala Ala Tyr Glu
                85                  90                  95
Gln His Lys Leu Glu Thr Met Asp Ser Leu Lys Gly Gly Lys Trp Ser
                100                 105                 110
Asn Gly Ala Glu Met Thr Glu Glu Ala Val Ala Glu Gln Gln Arg
                115                 120                 125
Met Phe Ala Glu Ala Arg Ala Arg Met Asn Gly Gly Ala Ile Ala Pro
                130                 135                 140
Lys Gln Gln Pro Glu Thr Asp Arg Ser Leu Glu Ser
145                 150                 155

<210> SEQ ID NO 22
<211> LENGTH: 103
<212> TYPE: PRT
<213> ORGANISM: Jatropha sp.

<400> SEQUENCE: 22

Met Glu Ser Glu Asn Val Glu Lys Val Val Ser Glu Ala Glu Glu Leu
 1               5                  10                  15
Pro Lys Ala Ile Val Arg Arg Ile Val Lys Asp Lys Leu Ser Gln Cys
                20                  25                  30
Ser Pro Asp Gly Asp Leu Ile Val His Lys Asp Ala Leu Val Ala Phe
                35                  40                  45
Ser Glu Ser Ala Arg Ile Phe Ile His Tyr Leu Ser Ala Thr Ala Asn
                50                  55                  60
Asp Ile Cys Lys Glu Ser Arg Arg Gln Thr Ile Asn Ala Asp Asp Val
 65                  70                  75                  80
Leu Lys Ala Leu Glu Glu Ile Glu Phe Pro Glu Phe Val Glu Pro Leu
                85                  90                  95
Lys Ala Ser Leu Lys Gly Lys
                100

<210> SEQ ID NO 23
<211> LENGTH: 122
<212> TYPE: PRT
<213> ORGANISM: Jatropha sp.

<400> SEQUENCE: 23

Met Thr Thr Leu Gly Phe Glu Glu Tyr Val Glu Pro Leu Lys Val Tyr
 1               5                  10                  15
Leu Gln Arg Phe Arg Glu Met Glu Gly Glu Lys Ala Ala Val Gly Arg
                20                  25                  30
Asp Lys Asp Ala Pro Gly Asn Gly Gly Pro Arg Val Arg Val Trp Trp
                35                  40                  45
Trp Ile Leu Gln Ser Asp Gly Arg Trp Tyr Trp Val Gly Glu Arg Cys
                50                  55                  60
Ile Asn His Gln Arg Arg Val His Val Asn Phe Ile Leu Arg Leu Gln
 65                  70                  75                  80
Glu Val Val Val Ser Met Tyr Met Cys Val Tyr Leu Ile Leu Val Met
```

```
                    85                  90                  95
Gly Lys Met Ile Gly Ser Thr Val Asp Asp Asp Asp Tyr Asn Arg
            100                 105                 110

Lys Leu Tyr Tyr Ala Cys Ala Ile Leu Ile
            115                 120

<210> SEQ ID NO 24
<211> LENGTH: 99
<212> TYPE: PRT
<213> ORGANISM: Jatropha sp.

<400> SEQUENCE: 24

Met Ser Lys Leu Gly Phe Asp Asp Tyr Ile Glu Pro Leu Thr Val Tyr
1               5                   10                  15

Leu His Arg Tyr Arg Glu Met Glu Gly Asp Arg Ser Ser Ile Arg Ser
            20                  25                  30

Glu Pro Leu Val Lys Arg Asn Val Glu Phe Gly Pro Leu Gly Val Ala
        35                  40                  45

Thr Ala Phe Ala Pro Ala Phe His Met Ser His His His Gly Phe
    50                  55                  60

Phe Gly Gly Ala Ala Ala Ala Met Gly Gly Tyr Thr Arg Asp Pro Ser
65                  70                  75                  80

Asn Ala Thr Ser Ser Gln His Ala Leu Ala Asn Gly Glu Ser Phe Gly
                85                  90                  95

Gln His Lys

<210> SEQ ID NO 25
<211> LENGTH: 97
<212> TYPE: PRT
<213> ORGANISM: Jatropha sp.

<400> SEQUENCE: 25

Met Pro Arg Ser Thr Val Arg Ser Leu Ala Lys Thr Ile Leu Asn Asp
1               5                   10                  15

Asp Thr Asn Ile Gln Lys Asp Ala Leu Thr Ala Leu Val Lys Gly Ser
            20                  25                  30

Thr Val Phe Ile Ser Tyr Leu Ala Ser His Ala Asn Glu Ile Ala His
        35                  40                  45

Ser Lys Lys Arg Lys Thr Ile Met Pro Asn Asp Val Phe Glu Ala Leu
    50                  55                  60

Lys Ile Ile Glu Tyr Asp Arg Phe Thr Ser Asp Leu Arg Glu Glu Phe
65                  70                  75                  80

Gly Glu Phe Pro Ala Lys Lys Val Gly Lys Ser Val Glu Ala Val Asp
                85                  90                  95

Asp

<210> SEQ ID NO 26
<211> LENGTH: 72
<212> TYPE: PRT
<213> ORGANISM: Jatropha sp.

<400> SEQUENCE: 26

Phe Asp Asn Tyr Ala Glu Ala Ile Val Arg Tyr Leu His Lys Tyr Arg
1               5                   10                  15

Glu Ala Glu Arg Glu Lys Ala Tyr Asn Asn Gln Asn Lys Ala Asn Pro
            20                  25                  30

Ser Asn Gln Glu Lys Asp Asp Asp Asn Gln Glu Ala Asn Ser Lys Ser
```

```
                35                  40                  45
Ser Ser Ser Gln Glu Gln Gln Gln Ile Asn Glu Thr Ile Pro Ser Thr
    50                  55                  60

Leu Glu Phe Arg Val Leu Glu Lys
65                  70
```

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaaaagcagg ctaaacaatg gctgattccg acaatgaatc tgga                44

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agaaagctgg gtcccttgaa ttgccggagc cacc                           34

<210> SEQ ID NO 29
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aaaaagcagg ctcaacaatg gttgacaatg caagcaataa ttcagac             47

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agaaagctgg gtaaaatcgc ctggaaacag aactgttatt gc                  42

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aaaaagcagg ctcaacaatg gaagaagaga gccatgccag tg                  42

<210> SEQ ID NO 32
<211> LENGTH: 37
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 32
agaaagctgg gtataacttc atatcttgcc aatgccc                            37

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aaaaagcagg ctcaacaatg aagcaaattt tgcctcctaa tgcaaaaatc              50

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agaaagctgg gtaagatggc cttgaacttc tagagctatt c                       41

<210> SEQ ID NO 35
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aaaaagcagg ctcaacaatg gctggaaaaa gaaaccaaat aaccagc                 47

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agaaagctgg gtagttatat ccatagccgc ttttaggagt aatta                   45

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggggacaagt ttgtacaaaa aagcaggct                                     29

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 38
ggggaccact ttgtacaaga aagctgggt                                    29

<210> SEQ ID NO 39
<211> LENGTH: 609
<212> TYPE: DNA
<213> ORGANISM: Jatropha sp.

<400> SEQUENCE: 39
atggctgatt ccgacaatga atctggagga cacaacaata acgcgaacag cgaactgtcg     60
gctcgcgaac aggacaggtt tttgccaatc gctaacgtta gcagaataat gaaaaaagct    120
ttgccggcca acgcgaagat ctcgaaagat gcaaaagaaa cggtgcagga gtgtgtatct    180
gaatttatca gctttattac cggagaagct tccgataagt gccagcgcga aaagcgaaag    240
acgattaacg gcgacgatct gctatgggct atgacgacgt taggttttga agagtacgtt    300
gagcctttaa agatttattt gcagaagtat agggagatgg aaggggagaa gagttctatg    360
ggaagacaag gagagaaaga tggtgctggt gggtctggtg gtggcggtgc cgccgcaggc    420
ggtggtgggt ccggtggagg agttagttct agtgcaggag gaggagctgg aggtggaggg    480
tttaatggcg gtggtcaagg gatgtatggt gggatgatga tgatgggaca tcatcaagga    540
cacatgtacg gctccggtgg gtatcatcag caaatgggta tcggaaaagg tggctccggc    600
aattcaagg                                                            609

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 40

His His His His His His
1               5
```

POLYNUCLEOTIDE ENCODING NF-YB DERIVED FROM JATROPHA AND USE THEREOF

CROSS-REFERENCE TO RELATED APPLICATIONS

This application is a Continuation of U.S. application Ser. No. 13/639,522, which is the National Stage of International Application No. PCT/JP2011/058026, filed Mar. 30, 2011, which claims priority to Japanese Application Nos. 2010-273463, filed Dec. 8, 2010, and 2010-090618, filed Apr. 9, 2010. The disclosure of application Ser. No. 13/639,522 and PCT/JP2011/058026 is expressly incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Nov. 26, 2012, is named P42720.txt and is 28,771 bytes in size.

TECHNICAL FIELD

The present invention relates to a polynucleotide encoding a NF-YB transcription factor as a novel gene of genus *Jatropha*, and use thereof, and in particular, use thereof for creating dry stress resistant *Jatropha*.

BACKGROUND ART

*Jatropha curcas* attracts attention as biological resources for production of biodiesel fuel because a non-edible *Jatropha* oil can be produced therefrom. Further, *Jatropha* is known as a plant that can be cultivated even at locations unsuited for growth of other crops in terms of water and inorganic nutrients, and is believed to be very beneficial for effective utilization of semi-arid regions and for greening. On the other hand, although *Jatropha* plants grow in barrens, production efficiency of oils by natural cultivating is not high because fruition of the plants is once a year and the size of the fruit is significantly smaller than that of palm. For this reason, development of highly productive *Jatropha* is demanded.

As one measure for improving the production efficiency of a *Jatropha* oil, a method of transforming *Jatropha* so that acetyl CoA carboxylase (ACCase) can be overexpressed for increasing the oil content of the seed is known, for example, as disclosed in Japanese National Patent Publication No. 2009-536029 (PTL 1).

On the other hand, from the view point of improving the productivity of *Jatropha* itself, it is also conceivable to impart drought tolerance that ensures high viability even under water deficient conditions.

Generally, growth of a plant is greatly influenced by environmental factors such as dryness, salt and low temperature, and hence development of agricultural crops imparted with environmental stress resistance is expected. As a dry stress resistant gene recombinant plant, the one wherein the stress responsive signaling intensity and mechanism are modified so as to be adaptive or responsive to dry stress, a method for improvement to achieve overproduction of a protein molecule involved in resistance (a protein responding to environmental stresses) and the like are conceivable.

Signaling pathways responsive to environmental stresses of plants are generally classified into pathways mediated by abscisic acid (ABA) which is a plant hormone, and pathways not mediated by ABA, and further sub-classified by the type of involved transcriptional regulators. Also as to proteins involved in response, regulatory proteins involved in response such as a transcription regulator, protease and protein kinase, and functional proteins responsible for resistance such as chaperone are known, and they are believed to take part in various physiological responses (Kazuo Shinozaki et al., Asakura Plant Physiology Course 5, "Environmental response", pp. 106-1145).

Abscisic acid (ABA) is a plant hormone that is involved in seed dormancy, opening/closing of stoma and osmotic stress resistance, and ABA is known to be deeply involved in expression of a group of stress responsive genes.

For example, NPL 1 (Wen-Xue Li et al., "The *Arabidopsis* NFYA5 Transcription Factor Is Regulated Transcriptionally and Posttranscriptionally to Promote Drought Resistance," The Plant Cell, Vol. 20: 2238-2251 (2008)) reports, in a mechanism of controlling dry stress resistance in *Arabidopsis thaliana*, that a NF-YA5 transcription factor is ABA-dependent and is strongly induced by dry stress, and that transformed *Arabidopsis thaliana* overexpressing NF-YA5 is superior to wild-type *Arabidopsis thaliana* in resistance to dry stress.

As a method of preparing environmental stress resistant *Arabidopsis thaliana*, Japanese Patent Laying-Open No. 2005-253395 (PTL 2) proposes a method of utilizing an activating function of a group of genes under the control of a transcription factor that activates transcription by binding with a cis element existing upstream the gene encoding a stress responsive protein expressed due to an environmental stress (a stress responsive transcription factor). Concretely, a SRK2C gene is disclosed as a novel gene encoding a signaling factor that induces expression of DREB/CBF which is a stress responsive transcription factor, and also it is disclosed that *Arabidopsis thaliana* transformed to overexpress the SRK2C gene shows dominantly high survival rate in comparison with a control even after stopping of water supply.

Further, NPL 2 (Donald E. Nelson et al., "Plant nuclear factor Y(NF-Y)B subunits confer drought tolerance and lead to improved corn yields on water-limited acres", PNAS, vol. 104, No. 42, 16450-16455 (2007)) reports that a corn NF-YB factor was identified, and a corn transformed by using this showed higher productivity under the condition of water shortage in comparison with the wild type.

Furthermore, in Japanese National Patent Publication No. 2009-540830 (PTL 3), as water deficient stress resistant plants of rice, corn, soybean and cotton, plants into which a transcription unit containing a promoter operably linked with DNA encoding a NF-YB protein of *Arabidopsis thaliana*, corn or soybean is introduced are disclosed. It is reported that by devising a promoter or the like, yield of the transformed plant modified to be able to overexpress NF-YB is improved in comparison with that of a wild-type control even under water deficient conditions.

CITATION LIST

Patent Literature

PTL 1: Japanese National Patent Publication No. 2009-536029
PTL 2: Japanese Patent Laying-Open No. 2005-253395

PTL 3: Japanese National Patent Publication No. 2009-540830

Non Patent Literature

NPL 1: Wen-Xue Li et al., "The *Arabidopsis* NFYA5 Transcription Factor Is Regulated Transcriptionally and Post-transcriptionally to Promote Drought Resistance", The Plant Cell, Vol. 20: 2238-2251 (2008)
NPL 2: Donald E. Nelson et al., "Plant nuclear factor Y(NF-Y)B subunits confer drought tolerance and lead to improved corn yields on water-limited acres", PNAS, vol. 104, No. 42, 16450-16455 (2007)

SUMMARY OF INVENTION

Technical Problem

A mechanism of signaling pathway for environmental stresses is complicated, and various transformation methods have been proposed for creating a dry stress resistant plant as described above. However, as to *Jatropha*, a regulatory protein related with dry stress, a functional protein related with resistance and the like have not been clarified.

It is an object of the present invention to create dry stress resistant *Jatropha* capable of ensuring high growth even under water deficient conditions, and to provide a gene or the like capable of transforming wild-type *Jatropha* to be dry stress resistant.

Solution to Problem

For achieving the object, as a result of examination of a gene for transforming *Jatropha* to be dry stress resistant, inventors of the present invention clarified a genomic sequence of *Jatropha*, and succeeded in isolating and identifying 13 genes encoding NF-YB, and accomplished the present invention. Specifically, the present invention is as follows.

[1] An isolated polynucleotide selected from the following polynucleotides:
(a) a polynucleotide represented by any one of SEQ ID NOs: 1 to 11;
(b) a polynucleotide encoding a NF-YB polypeptide derived from *Jatropha*, comprising a polynucleotide fragment represented by SEQ ID NO: 12 or 13; and
(c) a polynucleotide represented by a nucleotide sequence having a homology of 90% or higher with the nucleotide sequence of the polynucleotide of either one of (a) and (b), wherein a polypeptide encoded by the polynucleotide maintains dry stress resistance of the NF-YB polypeptide encoded by either one of the polynucleotides of (a) and (b).

[2] The isolated polynucleotide as described in [1] selected from the polynucleotides of (a) and (b).

[3] An isolated NF-YB polypeptide selected from the following polypeptides:
(a) a NF-YB polypeptide having an amino acid sequence represented by any one of SEQ ID NOs: 14 to 24;
(b) a NF-YB polypeptide derived from *Jatropha* comprising a polypeptide having an amino acid sequence represented by SEQ ID NO: 25 or 26; and
(c) a polypeptide represented by an amino acid sequence having a homology of 90% or higher with the amino acid sequence of the polypeptide of either one of (a) and (b), wherein the polypeptide maintains dry stress resistance of either one of the NF-YB polypeptides of (a) and (b).

[4] The isolated NF-YB polypeptide as described in [3] selected from the polypeptides of (a) and (b).

[5] A polynucleotide encoding the polypeptide as described in [3] or [4].

[6] A *Jatropha* plant transformation vector, wherein the polynucleotide as described in [1], [2] or [5] is incorporated.

[7] A transformant containing the vector as described in [6].

[8] A *Jatropha* plant transformed by using the vector as described in [6], wherein the plantlet is a dry stress resistant transformed *Jatropha* capable of overexpressing a NF-YB polypeptide compared with a wild type.

[9] A seed harvested from the dry stress resistant transformed *Jatropha* as described in [8].

[10] A method of producing a *Jatropha* oil by squeezing the seed as described in [9] and purifying it.

[11] A *Jatropha* oil produced by the production method as described in [10].

Advantageous Effects of Invention

When *Jatropha* is transformed by using the polynucleotide according to the present invention, the transformed *Jatropha* allows expression of a NF-YB polypeptide derived from *Jatropha* of the present invention, or a polypeptide equivalent thereto. With these polypeptides, it is possible to significantly improve the productivity of protein synthesis in which a NF-YB polypeptide is involved, and to significantly improve, for example, dry stress resistance.

DESCRIPTION OF EMBODIMENTS

Figure 1:
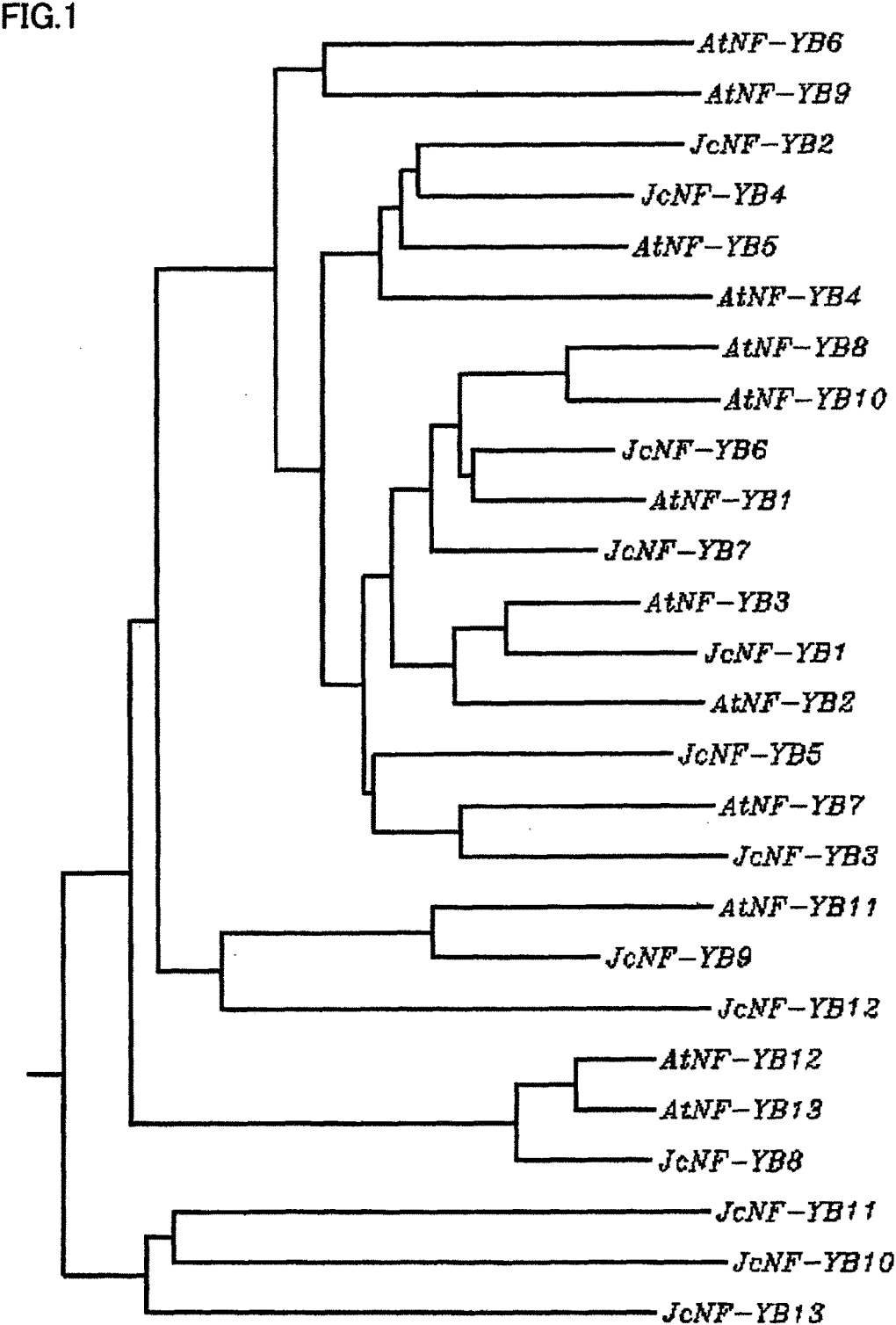
FIG. 1 is a chart showing a molecular phylogenetic tree of NF-YB of *Arabidopsis thaliana* and *Jatropha*.

[JcNF-YB Gene]
The isolated novel *Jatropha* gene according to the present invention is a polynucleotide encoding a wild-type transcription factor NF-YB of *Jatropha*, and is a family of 13 genes individually existing in a *Jatropha* genome. Concretely, the present invention includes (a) polynucleotides represented by SEQ ID NOs: 1 to 11 (named "JcNF-YB1 gene" to "JcNF-YB11 gene" sequentially); (b) polynucleotides encoding a NF-YB polypeptide derived from *Jatropha*, comprising polynucleotide fragments represented by SEQ ID NOs: 12 and 13 (respectively, named "JcNF-YB12 gene" and "JcNF-YB13 gene"); and (c) a polynucleotide represented by a nucleotide sequence having a homology of 90% or higher with the nucleotide sequence of the polynucleotide of either one of (a) and (b), wherein the polypeptide encoded thereby maintains dry stress resistance of the NF-YB polypeptide encoded by the polynucleotide of either one of (a) and (b). The nucleotide sequence of the polynucleotide of (c) has a homology of preferably 95% or higher, more preferably 98% or higher, and particularly preferably 99% or higher, with the nucleotide sequence of the polynucleotide of either one of (a) and (b).

Polypeptides that can be obtained by expression of each gene of the present invention include, for example, (a) NF-YB polypeptides of *Jatropha* wild-type transcription factors JcNF-YB1 to JcNF-YB11 (having amino acid sequences of SEQ ID NOs: 14 to 24); (b) NF-YB polypeptides derived from *Jatropha* comprising polypeptides having amino acid sequences represented by SEQ ID NOs: 25 and 26; and (c) a polypeptide represented by an amino acid sequence having a homology of 90% or higher with the amino acid sequence of the polypeptide of either one of (a) and (b), wherein the polypeptide maintains dry stress resistance of the NF-YB polypeptide of either one of (a) and (b). The polypeptide of (c) has a homology of preferably 95% or higher, more preferably 98% or higher, and particularly preferably 99% or higher, with the amino acid sequence of the polypeptide of either one of (a) and (b).

The nucleotide sequence of the gene of the present invention also includes polynucleotides encoding polypeptides of the above (a) to (c). For example, part of bases may be substituted as far as polypeptides of (a) and (b) are encoded, and in the JcNF-YB1 DNA represented by SEQ ID NO: 1, by substituting the sixth base G with the base T (SEQ ID NO: 39), it is possible to make the translation efficiency higher than that of the wild type.

Hereinafter, by the term "JcNF-YB gene", polynucleotides of the present invention are collectively referred to.

A method of preparing the JcNF-YB gene of the present invention is not particularly limited. For example, a PCR product of a target gene may be directly obtained by conducting a PCR reaction using a *Jatropha* genome as a template and primers designed for each JcNF-YB gene, or a PCR product of a target polynucleotide may be obtained by a RT-PCR method using the following primer set, from mRNA that is obtained by crushing part of a *Jatropha* plant, preferably leaves exposed to dry stress. Also, predetermined bases may be substituted, deleted or added according to an ordinary technique.

A method of directly obtaining a PCR product of a target gene using a *Jatropha* genome extracted according to a method of Sudheer et al., (Indian Journal of Biotechnology, Vol. 8 (2009) p. 187-192) is preferred. The method of Sudheer et al. has a feature in that NaCl concentration is regulated from in an extraction buffer to be used, to in a solution used for DNA precipitation, and that treatment in the purification step is conducted with Tris-saturated phenol, followed by a mixture of chloroform and isoamyl alcohol, and that 80% ethanol is used in the precipitation step.

mRNA may be prepared by a generally conducted method. For example, after grinding a frozen plant in a mortar or the like, a crude RNA fraction may be extracted and prepared from the obtained ground matter by a glyoxal method, a guanidine thiocyanate-cesium chloride method, a lithium chloride-urea method, a proteinase K-deoxyribonuclease method or the like. Also, a commercially available kit may be used.

Determination and confirmation of a nucleotide sequence of an obtained PCR product may be conducted by a conventionally known method, for example, a Maxim-Gilbert chemical modification method or a dideoxynucleotide chain termination method using M13 phage.

[Creation of Dry Stress Resistant Transformed *Jatropha*]

The dry stress resistant transformed *Jatropha* of the present invention is created by gene introduction of an expression cassette having the JcNF-YB gene operably linked with a promoter for expression or expression regulation, into a wild-type *Jatropha*.

The species of *Jatropha* intended by the present invention are not particularly limited, and *Jatropha curcas, Jatropha potagurica, Jatropha multifida, Jatropha berlandieri, Jatropha integerrima* and the like may be used. Among these, from the view point of large oil content, *Jatropha curcas* is preferably used.

The gene introduction may be achieved by any method including methods of directly introducing DNA into a cell such as a method of fusing protoplasts, an electroporation method and a gene shotgun method; and methods of indirectly introducing DNA by using *Agrobacterium tumefaciens* or *R. rhizogenes*, and a method of using an *agrobacterium* is preferred. In the following, a transformation method using an *agrobacterium* is described.

An *agrobacterium* is a plant pathogen, and has a Ti plasmid having a region sandwiched between LB (left border) and RB (right border) (a T-DNA (Transferred DNA) region) that can be cut out and inserted into a host genome. When a host plant is infected with an *agrobacterium* having a plasmid incorporating a gene to be introduced, namely a JcNF-YB gene in this T-DNA region, the T-DNA region is cut out, and forms a complex with a protein group encoded by a vir region, and enters a plant cell, and further insertion into a host genome is achieved.

As a transformation method using an *agrobacterium*, a binary vector method is preferred. The binary vector method is a method of inserting a target gene into a plant genome by introducing into an *agrobacterium*, a plasmid having a target exogenous gene incorporated into a T-DNA region of a plasmid having borders (LB and RB) of the T-DNA region, in addition to a T-DNA-deficient plasmid of a Ti plasmid (such as pAL4404), and infecting a plant with the *agrobacterium*.

An expression cassette used for creation of transformed *Jatropha* using the binary vector method includes the JcNF-YB gene according to the present invention, a promoter for expression of the nucleotide, a marker gene and a reporter gene in the T-DNA region.

As a promoter, a 35S cauliflower mosaic virus promoter, a nopaline synthase (NOS) promoter, and other endosperm-specific promoters such as β phaseolin, napin and ubiquitin can be recited.

As a selection marker gene, a gene that imparts resistance to a selection agent such as an antibiotic or a herbicide is used. Concrete examples thereof include a kanamycin resistant gene, a paromomycin B resistant gene, or a resistant gene against herbicides such as glufosinate and glyphosate. Also usable is a gene that expresses a selection marker enabling visual identification of a transformant, for example, a chromogenic or fluorescent protein such as luciferase or green fluorescent protein (GFP), or a gene that expresses β glucuronidase or GUS for which various chromogenic substrates are known. Such a selection marker may be used also as a reporter gene.

If necessary, an enhancer, a terminator, a tag and the like may further be included. An enhancer is used for improving expression efficiency of a target gene, and for example, an enhancer region including an upstream sequence in a CaMV 35S promoter can be recited. A terminator may be any sequence capable of terminating transcription of a gene transcribed by a promoter, and for example, a terminator of a nopaline synthase (NOS) gene, and a terminator of an octopine synthase (NOS) and a CaMV 35S RNA gene are recited.

As a binary vector for use in transformation of *Jatropha* by the binary vector method, those including the aforementioned expression cassette in a T-DNA region, and concretely, those prepared by incorporating the aforementioned expression cassette into commercially available vectors such as pBI series, pPZP series, pSMA series, and pGWB series may be used. In particular, a binary vector for plant transformation to which a cloning system of Gateway (registered trade name) is applicable is preferred, and as such a vector, pGWB series vectors can be recited. In these pGWB series vectors, a target gene and a reporter are operably linked using a cauliflower mosaic virus (CaMV) 35S promoter as a promoter; a hygromycin resistant gene or a kanamycin resistant gene as a selection marker gene; β-glucuronidase (GUS), green fluorescent protein (GFP), luciferase (LUC), yellow fluorescent protein (YFP), or cyan fluorescent protein (CFP) as a reporter; and 6xHis (SEQ ID NO: 40), FLAG, 3xHA, 4xMyc, GST, or T7-epitope as a tag. Further, there are sequences that encode a reporter and a tag for allowing fusion at both the N terminal and the C terminal.

The Gateway (registered trade name) cloning system facilitates construction of an expression vector by using the Gateway (registered trade name) signal (att). In this method, by a reaction (BP reaction) between a donor vector having attP1 and attP2 sequences, and a target gene having attB1 and attB2 sequences added on each terminal, an entry vector having the target gene incorporated therein (having attL1 and attL2 sequences on each terminal) is created, and then by a recombination reaction (LR reaction) between this entry vector and a destination vector having a promoter required for expression incorporated therein (added with attR1 and attR2 sequences), a vector having the target gene inserted therein (expression vector) is created.

Therefore, first, a cloned JcNF-YB gene is allowed to undergo a BP reaction with a donor vector to prepare an entry vector having cloned JcPPAT cDNA incorporated in the donor vector, and then by a LR reaction between the entry vector and a destination vector (pGWB), an expression vector having the target DNA (JcNF-YB) incorporated therein can be created.

A detailed description for construction of an expression cassette for plant transformation using the Gateway binary vector (pGWB) is found in Nakagawa et al., "Development of Series of Gateway Binary Vectors, pGWBs, for Realizing Efficient Construction of Fusion Genes for Plant Transformation", Journal of Bioscience and Bioengineering, Vol. 104, No. 1, 34-41 (2007).

The expression vector created as described above (plant transformation vector) can be amplified in *Escherichia coli*. The amplified transformation vector may be introduced into an *agrobacterium* by an electroporation method or the like. The *agrobacterium* into which the expression vector is introduced in this manner is used for transformation of *Jatropha*.

Introduction of a target gene (JcNF-YB gene) into *Jatropha* by infection of an *agrobacterium* having the plant transformation vector can be achieved by using a known method such as a leaf disc method.

Concretely, a bacterial liquid for infection in which an *agrobacterium* is suspended in a MS medium is prepared, and the bacterial liquid and part of *Jatropha* which is a host (preferably, cut pieces of cotyledons, hereinafter referred to as "*Jatropha* leaf pieces") are co-cultivated for about 3 days. The leaf pieces of *Jatropha* are dipped in a MS medium for about 2 days prior to the co-cultivation, and are preferably sonicated. In this way, it is possible to improve the efficiency of introduction. Also preferred is a Sandvortex method that applies vibration to a suspension of an *agrobacterium* into which sand has been added because infectability of the *agrobacterium* is improved.

As a co-cultivation medium, a MS medium or the like incorporating a plant hormone such as 3-indolebutyric acid (IBA) or 6-benzylaminopurine (BA) is used.

Following the co-cultivation, the *Jatropha* leaf pieces are washed, and transferred into a selection medium (containing an antibiotic corresponding to the selection marker gene used in the expression cassette in the transformation vector), and incubated, and then calluses formed in the leaf pieces are cut out, and transferred to a selection medium, and further screening of the transformed *Jatropha* (recombinant cell) is conducted.

As the selection medium, the one prepared by adding an antibiotic (kanamycin, hygromycin) which is a substance for selection to the medium (MS medium or the like) used for pre-culture, which contains IBA, BA, thidiazuron (TDZ) or the like as a plant hormone is preferably used.

Next, the selected calluses are transferred into a medium such as a RI medium or a MS medium, and allowed to root and redifferentiate into a plantlet. Induction of redifferentiation can be achieved by appropriately setting kinds and quantities of various ingredients including plant growth regulation substances such as auxin and cytokinin, and carbon sources in the medium, and light, temperature and so on.

[Transformed *Jatropha*]

The transformed *Jatropha* of the present invention is able to overexpress a transcription product of a JcNF-YB gene from a gene encoding a transcription factor JcNF-YB involved in transcription of a dry stress resistant gene, in comparison with the wild type. Therefore, it is possible to activate transcription and expression of the dry stress resistant gene. As a result, even in a dry condition, higher plant growth is achieved in comparison with the wild type.

The transformed plant of the present invention embraces not only "T1 generation" subjected to the transformation treatment, but also progeny plants including "T2 generation" which are succeeding generations obtained from a seed of this plant, and a next generation (T3 generation) obtained by self-fertilization of a flower of the plant of "T2 generation" which is proved to be a transformant by drug selection or analysis by a Southern method or the like.

[Production of *Jatropha* Oil]

A *Jatropha* oil can be produced from a seed harvested from the transformed *Jatropha* of the present invention according to a routine method. For example, a *Jatropha* oil that can be used as biodiesel can be produced by obtaining a material oil by squeezing a seed, and filtering the material oil through a filter. When the *Jatropha* oil is intended to be further purified, for example, it can be purified by distillation, and phorbol ester can be removed by the method described in Japanese Patent Laying-Open No. 2010-209177.

EXAMPLES

Embodiments for practicing the present invention will be described by way of examples. The following examples are not given to limit the scope of the present invention.
[Isolation of JcNF-YB-Encoding DNA in *Jatropha* and Construction of Transformation Plasmid]
(1) Preparation of *Jatropha* Genomic DNA Thailand line *Jatropha* (*Jatropha curcas*) distributed from the agricultural department of Tottori University was used. From mature leaves of this *Jatropha*, genomic DNA was prepared according to the method of Sudheer et al. (Indian Journal of Biotechnology, Vol. 8 (2009) p 187-192).

The leaves of *Jatropha* were washed with distilled water, and the moisture was blotted with tissue paper, and 1 g was ground into powder in a mortar. The resultant powder was sufficiently mixed with 10 mL of an extraction buffer (2% CTAB, 100 mM Tris-HCl, 3.5 M NaCl, 20 mM EDTA, 1% β-mercaptoethanol) at 65° C. The mixture was incubated in a water bath at 65° C. for 90 minutes, and then cooled for 5 minutes. An equivalent amount of a mixture of chloroform and isoamyl alcohol (24:1) was added, and slowly mingled to give a uniform emulsion. This emulsion was centrifuged at 10,000×g for 15 minutes, and then the water phase was separated. The separated water phase was again added with an equivalent amount of a mixture of chloroform and isoamyl alcohol (24:1) and slowly mingled to give a uniform emulsion. After centrifuging this emulsion at 10,000×g for 15 minutes at 4° C., the water phase was collected. The collected water phase was added with an equivalent amount of isopropyl alcohol, and cooled at −20° C. for 30 minutes, and then centrifuged at 10,000×g for 30 minutes at 4° C. to obtain a DNA pellet. This DNA pellet was washed with 70% ethanol, and then suspended again in a TE buffer. The obtained DNA pellet was dissolved in a TE buffer (10 mM Tris-HCl, 1 mM EDTA, pH 8.0) containing 20 mg/mL of RNase to give a genomic DNA sample.

The obtained extracted genomic DNA was fragmented by culturing together with EcoRI, HindIII and SauIII, and sequenced by a sequencer.

(2) Cloning and amplification of JcNF-YB-encoding gene

Based on the genome information (Contig Map) of *Jatropha* obtained from (1), a gene showing a homology with *Arabidopsis thaliana* NF-YB was searched by TBLASTN. For gene information of NF-YB of *Arabidopsis thaliana*, gene registration information of NCBI (www.ncbi.nlm.nih.gov/sites/entrez?db=gene&cmd=Retrieve&dopt=full_rep ort&list_uids=818472&itool=HomoloGeneMainReport) was referred to.

As a result of search, those annotated as encoding JcNF-YB are as follows.
Contig1977.1.1
Contig21632.1.1
Contig30054.1.1
Contig31310.1.2
Contig31788.1.2
Contig3182.1.1
Contig8131.1.1
F4IDXKH14IHOZQ.1
HYB_Contig17630.1.2
HYB_Contig31673.1.1
HYB_Contig46618.1.1
HYB_Contig46864.1.1
HYB_Contig61720.1.1.1
Jatropha454_3 Run_c74008.1

Among these sequences, since DNA nucleotide sequences of HYB_Contig46618.1.1 and HYB_Contig61720.1.1.1 are proved to perfectly coincide with each other except for the terminal parts, we decided to use HYB_Contig46618.1.1 for prediction of a JcNF-YB gene. Therefore, it is supposed that 13 kinds of NF-YB genes are present in *Jatropha* (these genes are named NF-YB1 to NF-YB13). As a result of homology search, relations between *Jatropha* DNA contained in each of the above genome fragments and an *Arabidopsis thaliana* NF-YB gene are as shown in Table 1. Nucleotide sequences of JcNF-YB genes are shown in SEQ ID NOs: 1 to 13 in the sequence list. Amino acid sequences of polypeptides obtained by translating these polynucleotides are sequentially shown in SEQ ID NOs: 14 to 26. Further, CLASTALW analysis was conducted for JcNF-YB1 to JcNF-YB13 and NF-YB family of *Arabidopsis thaliana* (AtNF-YB1 to AtNF-YB13), and a molecular phylogenic tree was prepared. The result of preparation is shown in FIG. 1.

TABLE 1

| *Jatropha* genomic DNA | Novel isolated NF-YB gene name of *Jatropha* | NF-YB gene of *Arabidopsis thaliana* showing highest homology |
|---|---|---|
| Contig8131.1.1 | JcNF-YB1 | AtNF-YB3 |
| Contig3182.1.1 | JcNF-YB2 | AtNF-YB5 |
| Contig31310.1.2 | JcNF-YB3 | AtNF-YB7 |
| Contig1977.1 | JcNF-YB4 | AtNF-YB5 |
| HYB_Contig46864.1.1 | JcNF-YB5 | AtNF-YB3 |
| Contig21632.1.1 | JcNF-YB6 | AtNF-YB1 |
| HYB_Contig17630.1.2 | JcNF-YB7 | AtNF-YB1 |
| Contig31788.1.2 | JcNF-YB8 | AtNF-YB13 |
| HYB_Contig46618.1.1 | JcNF-YB9 | AtNF-YB11 |
| HYB_Contig31673.1 | JcNF-YB10 | AtNF-YB2 |
| Contig30054.1 | JcNF-YB11 | AtNF-YB6 |
| F4IDXKH14IHOZQ | JcNF-YB12 | AtNF-YB11 |
| jatropha454_3Run_c74008 | JcNF-YB13 | AtNF-YB4 |

Next, JcNF-YB1 to JcNF-YB5 genes were amplified by conducting a PCR reaction using *Jatropha* (Thailand line breed) genomic DNA as a template, and respective primer sets (SEQ ID NOs: 27 to 36) shown in Table 2.

TABLE 2

| Target gene | | Forward primer | | Reverse primer |
|---|---|---|---|---|
| NF-YB1 | SeqID:27 | 5'-AAAAAGCAGGCTAAACAATGGCT GATTCCGACAATGAATCTGGA -3' | SeqID:28 | 5'-AGAAAGCTGGGTCCCTTGAATT GCCGGAGCCACC -3' |
| NF-YB2 | SeqID:29 | 5'-AAAAAGCAGGCTCAACAATGGTT GACAATGCAAGCAATAATTCAGAC -3' | SeqID:30 | 5'-AGAAAGCTGGGTAAAATCGCC TGGAAACAGAACTGTTATTGC -3' |
| NF-YB3 | SeqID:31 | 5'-AAAAAGCAGGCTCAACAATGGAA GAAGAGAGCCATGCCAGTG -3' | SeqID:32 | 5'-AGAAAGCTGGGTATAACTTCAT ATCTTGCCAATGCCC -3' |
| NF-YB4 | SeqID:33 | 5'-AAAAAGCAGGCTCAACAATGAAG CAAATTTTGCCTCCTAATGCAAAAAT C -3' | SeqID:34 | 5'-AGAAAGCTGGGTAAGATGGCC TTGAACTTCTAGAGCTATTC -3' |
| NF-YB5 | SeqID:35 | 5'- AAAAAGCAGGCTCAACAATGGCT GGAAAAAGAAACCAAATAACCAGC- 3' | SeqID:36 | 5'-AGAAAGCTGGGTAGTTATATCC ATAGCCGCTTTTAGGAGTAATTA- 3' |

The reaction liquid used for PCR is as follows.
1.25 Unit Ex tag (TAKARA BIO)
1× Ex tag buffer (TAKARA BIO)

0.2 mM dNTPs (TAKARA BIO)
1 µM Forward primer
1 µM Reverse primer

The reaction liquid prepared in the above was added with 1 µL of a *Jatropha* genomic DNA solution diluted 100 folds to make the total amount 50 µL, and a PCR reaction was conducted under the following conditions.

After retaining at 96° C. for 5 minutes, a cycle of [96° C., 30 seconds→60° C., 30 seconds→72° C., 1 minute] was repeated 30 times, and then the reaction was retained at 72° C. for 5 minutes, and cooled to 4° C.

Figure 2:
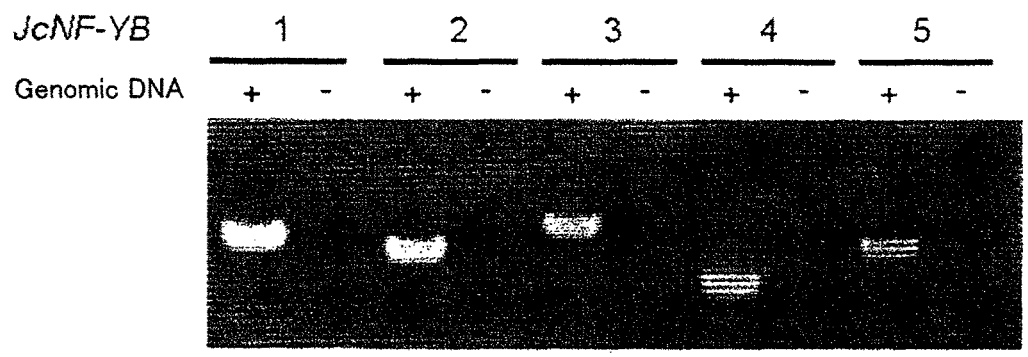
FIG. 2 is a photograph showing a result of agarose electrophoresis of NF-YB1 to NF-YB5.

After end of the reaction, DNA obtained by amplification was identified by agarose gel electrophoresis. Results of electrophoresis of JcNF-YB1 to JcNF-YB5 are shown in FIG. 2. Further, sequences of the obtained PCR products were determined by a DNA sequencer. Respective nucleotide sequences of JcNF-YB1 to JcNF-YB5 polynucleotides are as shown in SEQ ID NOs: 1 to 5 in the sequence list.

For applying a Gateway (registered trade name) cloning system for DNA represented by SEQ ID NO: 1 (JcNF-YB1), a PCR reaction for adding the following adaptor sequences attB1 (SEQ ID NO: 37) and attB2 (SEQ ID NO: 38) was conducted.

[Chemical formula 1]
attB1: 5' - GGGGACAAGTTTGTACAAAAAAGCAGGCT -3' attB2: 5' - GGGGACCACTTTGTACAAGAAAGCTGGGT-3'

The PCR reaction was conducted with the one prepared by adding each 1 µL of a DNA solution to the following reaction liquids to make the total amount 50 µL.
1.25 Unit Ex taq (TAKARA BIO)
1× Ex taq buffer (TAKARA BIO)
0.2 mM dNTPs (TAKARA BIO)
1 µM attB1_adapter
1 µM attB2_adapter The PCR reaction was conducted with the following temperature cycle. After retaining at 94° C. for 1 minute, a cycle of [94° C., 15 seconds→45° C., 30 seconds→68° C., 1 minute] was repeated 5 times, and then a cycle of [94° C., 15 seconds→55° C., 30 seconds→68° C., 1 minute] was repeated 20 times, and then the reaction was cooled to 4° C. After end of the reaction, amplified DNA was checked by agarose electrophoresis.

(3) Construction of Transformation Plasmid

A JcNF-YB1 gene was cloned by using a donor vector (pDONR221) of the Gateway (registered trade name) system of Invitrogen. Concretely, by conducting a recombination reaction (BP reaction) using BP Clonase (Invitrogen) after mixing the JcNF-YB1 gene (having attB1 and attB2 on each terminal) amplified in the above by PCR and the donor vector pDONR221, pENTRJcNF-YB1 which is to be an entry vector was obtained, and introduced into an *Escherichia coli* DH5α strain. pDONR221 has a kanamycin resistant gene introduced as a marker gene.

For construction of a plasmid for plant transformation, a pENTRJcNF-YB1 plasmid was extracted from the *Escherichia coli*, and mixed with a plasmid vector (destination vector) pGWB11 that was straight-chained by a restriction enzyme XhoI (TAKARA BIO), and then a recombination reaction was conducted using LR Clonase (Invitrogen).

Figure 3:
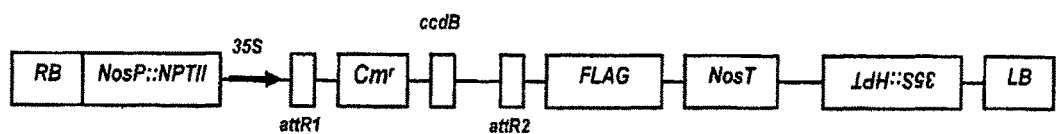
FIG. 3 is a gene map of a pGWB11 plasmid (see Nakagawa et al., "Development of Series of Gateway Binary Vectors, pGWBs, for Realizing Efficient Construction of Fusion Genes for Plant Transformation", Journal of Bioscience and Bioengineering Vol. 104 (2007), No. 1 p. 38).

As shown in FIG. 3, pGWB11 has a 35S promoter as a promoter, and has a FLAG tag added to its C terminal. Also, a 35S promoter -R1-Cmr-ccdB-R2-FLAG is inserted between HindIII and SacI. The part of R1-Cmr-ccdB-R2 can be substituted by attB1-(PPAT)-attB2 by the LR reaction with the entry vector. In this manner, pGWB11JcNF-YB1 which is to be a vector for plant recombination was obtained.

[Creation of Transformant]

(1) Preparation of *Agrobacterium* for Transformation

The aforementioned vector for recombination was introduced into an *agrobacterium* by an electroporation method to achieve transformation. This transformed *agrobacterium* was shake-cultured in a YEB liquid medium (added with 50 mg/L kanamycin, 50 mg/L hygromycin) at 30° C. for 2 days, and then harvested by centrifugation. The harvested bacterial cells were resuspended in the YEB medium, to prepare a bacterial liquid for infection.

(2) Transformation of *Jatropha*

As a *Jatropha* cell which is to be a host, Thailand line of *Jatropha* (*Jatropha curcas*) which is the same species of *Jatropha* as that used for genome extraction was used. Using mature leaves of the *Jatropha*, transformation was conducted by a leaf disc method. Concretely, first, cut pieces of mature leaves of *Jatropha* which are to be a host (about 25 mm², hereinafter, referred to as a "*Jatropha* leaf pieces") is sterilized with diluted kitchen bleach, and kept still at 25° C. for 2 days on a Pre-conditioning agar medium prepared by adding plant hormones (TDZ, IBA, BA) to a MS basal medium. A bacterial liquid for infection is prepared by suspending an *agrobacterium* in a MS medium, and the aforementioned *Jatropha* leaf pieces are dipped in the bacterial liquid, and shaken for 10 minutes. Then, co-cultivation is conducted on an agar medium at 25° C. for 3 days in a light-shielded environment. As a co-cultivation medium, a Co-cultivation medium prepared by adding acetosyringone to a Pre-conditioning medium is used.

(3) Screening of Transformed *Jatropha*

A transformant having the expression cassette prepared in the above stably inserted into a chromosomal genome of *Jatropha* is screened.

Concretely, *Jatropha* leaf pieces after co-cultivation are washed with an aqueous solution of cefotaxime sodium (200 mg/L), and transformed *Jatropha* (a recombinant cell) is screened. As an antibiotic for screening, kanamycin (20 mg/L) is used. Following transfer to a Shoot regeneration I agar medium (SR-I), the leaf pieces in which formation of calluses are observed after culturing at 25° C. are transferred to a Shoot regeneration II (SR-II) agar medium.

Next, the selected calluses are transferred to a Shoot elongation I agar medium (SE-I) and a Shoot elongation II agar medium (SE-II), and an embryoid is allowed to differentiate, and rooting is induced in the Root induction agar medium (RI), to obtain a redifferentiated *Jatropha* plant (T1).

A culture medium composition used herein is shown below.

| <MS basal medium> | |
|---|---|
| MS | 1×, (pH 5.8) |
| Sucrose | 3% |
| Myo-inositol | 100 mg/L |
| Thiamine hydrochloride (pH 5.8) | 10 mg/L |
| Agar | 0.8% |
| <Pre-conditioning medium> | |
| MS basal medium | |
| Thidiazuron (TDZ) | 0.5 mg/L |
| 6-benzylaminopurine (BA) | 1 mg/L |
| 3-indole butyric acid (IBA) | 0.075 mg/L |

| <Co-cultivation medium> MS basal medium | |
|---|---|
| Thidiazuron (TDZ) | 0.5 mg/L |
| 6-benzylaminopurine (BA) | 1 mg/L |
| 3-indole butyric acid (IBA) | 0.075 mg/L |
| Acetosyringone (AS) | 20 mg/L |
| <SR-I medium> MS basal medium | |
| Thidiazuron (TDZ) | 0.5 mg/L |
| 6-benzylaminopurine (BA) | 1 mg/L |
| 3-indole butyric acid (IBA) | 0.075 mg/L |
| Cefotaxime sodium | 200 mg/L |
| Kanamycin | 20 mg/L |
| <SR-II medium> MS basal medium | |
| 6-benzylaminopurine (BA) | 3 mg/L |
| 3-indole butyric acid (IBA) | 0.5 mg/L |
| Cefotaxime sodium | 200 mg/L |
| Kanamycin | 20 mg/L |
| <SE-I medium> MS basal medium | |
| 6-benzylaminopurine (BA) | 2 mg/L |
| Cefotaxime sodium | 200 mg/L |
| Kanamycin | 20 mg/L |
| <SE-II medium> MS basal medium | |
| 6-benzylaminopurine (BA) | 2 mg/L |
| Kanamycin | 20 mg/L |
| <RI medium> | |
| MS basal medium (MS of ½ concentration) | |
| 3-indole butyric acid (IBA) | 0.2 mg/L |

(4) Confirmation of JcNF-YB Gene Expression

It is checked that JcNF-YB1 transcription factor is overexpressed in a transformant selected by the screening.

A transformed cell (transformed dicotyledonous cell that expresses a NF-YB polypeptide by a promoter) and a control (dicotyledonous cell of wild-type *Jatropha*) are respectively cultured, and mRNA is extracted. The amount of mRNA of JcNF-YB1 transcription factor of the transformed cell is compared with that in the control.

(5) Confirmation of Dry Stress Resistance of Transformed *Jatropha*

A transformed plantlet obtained by redifferentiation is sand cultured, and cultured under a water deficient condition after irrigation is stopped at an arbitrary point of time, and the photosynthetic rate and chlorophyll fluorescence, transpiration rate, and yellowing, curling and falling of mature leaves of the transformed plantlet are compared with those of the wild type, and dry stress resistance is evaluated.

INDUSTRIAL APPLICABILITY

The novel isolated gene of the present invention can be used for creation of dry stress resistant *Jatropha*, and hence *Jatropha* capable of growing in a dry area can be provided.

The invention claimed is:

1. A vector comprising a heterologous nucleotide sequence and a polynucleotide with at least 99% identity to SEQ ID NO:6, wherein expression of the polynucleotide enhances stress resistance in *Jatropha* compared to wild-type *Jatropha*.

2. The vector according to claim 1, comprising SEQ ID NO:6.

3. The vector according to claim 1, which is a *Jatropha* plant transformation vector.

4. A transgenic *Jatropha* plant containing the vector according to claim 3.

5. A transgenic *Jatropha* plant transformed with the vector according to claim 3, wherein the transgenic *Jatropha* plant has increased stress resistance compared to a corresponding control *Jatropha* plant.

6. A method for preparing a stress resistant *Jatropha* plant, said method comprising: preparing an isolated polynucleotide with at least 99% identity to SEQ ID NO:6, wherein expression of the polynucleotide enhances stress resistance in *Jatropha* compared to wild-type *Jatropha*;

preparing a *Jatropha* plant transformation vector comprising said isolated polynucleotide;

and transforming a *Jatropha* plant with said vector.

* * * * *